(12) United States Patent
Fukuoka

(10) Patent No.: US 10,259,792 B2
(45) Date of Patent: Apr. 16, 2019

(54) CRYSTAL OF URACIL COMPOUND

(71) Applicant: TAIHO PHARMACEUTICAL CO., LTD., Chiyoda-ku (JP)

(72) Inventor: Masayoshi Fukuoka, Tokushima (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/570,779

(22) PCT Filed: Apr. 28, 2016

(86) PCT No.: PCT/JP2016/063495
§ 371 (c)(1),
(2) Date: Oct. 31, 2017

(87) PCT Pub. No.: WO2016/178416
PCT Pub. Date: Nov. 10, 2016

(65) Prior Publication Data
US 2018/0134666 A1    May 17, 2018

(30) Foreign Application Priority Data

May 1, 2015    (JP) ................................ 2015-093862

(51) Int. Cl.
*A61P 35/00*   (2006.01)
*C07D 239/22*  (2006.01)
*C07D 239/54*  (2006.01)

(52) U.S. Cl.
CPC ............ *C07D 239/22* (2013.01); *A61P 35/00* (2018.01); *C07D 239/54* (2013.01); *C07B 2200/13* (2013.01)

(58) Field of Classification Search
CPC ... A61P 35/00; C07B 2200/13; C07D 239/22; C07D 239/54
See application file for complete search history.

(56) References Cited

U.S. PATENT DOCUMENTS

2011/0082163 A1* 4/2011 Fukuoka ............... C07D 239/46
                                                  514/274
2012/0225838 A1* 9/2012 Fukuoka ............... A61K 31/513
                                                  514/50

FOREIGN PATENT DOCUMENTS

| EP | 2 295 414 A1 | 3/2011 |
| EP | 2 508 185 A1 | 10/2012 |
| WO | 2009/147843 A1 | 12/2009 |
| WO | 2011/065541 A1 | 6/2011 |

OTHER PUBLICATIONS

Chen et al. (Cryst. Growth Des 2011, 11, 887-895) (Year: 2011).*
Kawahara et al (J. Clin. Pathol. 2009, 62, 364-69, published online Dec. 3, 2008) (Year: 2008).*
Trisha Gura, Science, Nov. 1997 (Year: 1997).*
Merck Manual (Year: 1992).*
International Search Report dated Jul. 5, 2016, in PCT/JP2016/063495, filed Apr. 28, 2016.
Noriaki Hirayama, "Yuki Kagobustu Kesho Sakusei Handbook", Tokyo: Kodansha Ltd., 2008. 67 pages, with partial English translation.
Masakuni Matsuoka, "Advanced Crystallization Technology of Organic Materials—Control of Size, Morphology, Polymorph and Purity—", Pharm Tech Japan, vol. 19, No. 6, May 1, 2003, 18 pages, with partial English translation.
Ministry of Health and Welfare Iyakuhin Anzenkyoku Shinsa Kanri Kacho, Iyakushin. No. 308, 1998, 12 pages, with partial English translation.
Shozo Asahara, et al., "Yozai Handbook", Tokyo: Kodansha Ltd., 1985, pp. 46-51, with partial English translation (5 sheets).
Yoshihisa Matsuda, "Farumashia," Pharmaceutical Society of Japan vol. 43, No. 2, 2007, pp. 111-116, with partial English translation (7 sheets).
Yusaku Shioji, "Kokei Seizai no Seizo Gijutsu", Trade edition, Tokyo: CMC Publishing Co., Ltd., Jan. 27, 2003, 5 pages, with partial English translation.
Extended European Search Report dated Oct. 16, 2018 in corresponding European Patent Application No. 16789552.3 citing documents AO, AP and AX therein, 7 pages.
Mino R. Caira, "Crystalline Polymorphism of Organic Compounds", Topics in Current Chemistry, vol. 198, XP008166276, Jan. 1, 1998, pp. 163-208.

* cited by examiner

*Primary Examiner* — Umamaheswari Ramachandran
(74) *Attorney, Agent, or Firm* — Oblon, McClelland, Maier & Neustadt, L.L.P.

(57) ABSTRACT

The present invention provides a crystal that has preferable oral absorption and can be obtained with particularly preferable reproducibility. Provided is a crystal of (R)—N-(1-(3-(cyclopentyloxy)phenyl)ethyl)-3-((2,4-dioxo-3,4-dihydropyrimidin-1(2H)-yl)methoxy)propane-1-sulfonamide.

8 Claims, 3 Drawing Sheets

CRYSTAL OF URACIL COMPOUND

FIELD OF THE INVENTION

The present invention relates to a novel crystal of a uracil compound. More specifically, the present invention relates to a novel crystal of a uracil compound which can be stably supplied in a highly reproducible manner as a crystal of a drug substance for use in the production of a medicine and has superior absorbability, and a pharmaceutical composition which contains the same as an active ingredient and is useful as an antitumor effect potentiator.

BACKGROUND OF THE INVENTION

Generally, in the case of using a compound as an active ingredient of a pharmaceutical product, a single crystal form having certain qualities needs to be stably obtained in a highly reproducible manner. It is also preferable that the resulting single crystal form has superior absorbability.

Meanwhile, (R)—N-(1-(3-(cyclopentyloxy)phenyl)ethyl)-3-((2,4-dioxo-3,4-dihydropyrimidin-1(2H)-yl)methoxy)propane-1-sulfonamide (hereinafter also referred to as "compound (1)") represented by formula (1) below:

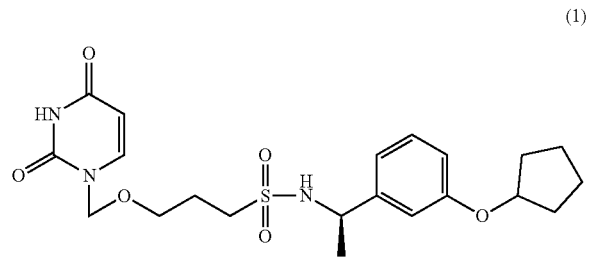 [SMILES: C[C@@H](NS(=O)(=O)CCCOCn1ccc(=O)[nH]c1=O)c1cccc(OC2CCCC2)c1]

(1)

is described in Patent Document 1 as a compound having deoxyuridine triphosphatase inhibitory activity. Moreover, Patent Document 2 discloses that compound (1) above potentiates the antitumor effects of anticancer agents and is currently under clinical development.

As for the manufacturing method of compound (1), the resulting reaction product was purified by silica gel column chromatography, and the resulting form was a foam (amorphous).

Hence, a crystal form of compound (1), which is preferable as a crystal of a drug substance for use in the production of a pharmaceutical product, is completely unknown.

CITATION LIST

Patent Document

Patent Document 1:
International Publication No. WO 2009/147843
Patent Document 2:
International Publication No. WO 2011/065541

SUMMARY OF THE INVENTION

Problems to be Solved by the Invention

An object of the present invention is to provide a crystal of compound (1) useful as, for example, an antitumor effect potentiator, which has superior absorbability and storage stability as a drug substance for use in the production of a pharmaceutical product and can be obtained preferably in a highly reproducible manner.

Means for Solving the Problems

The inventors have conducted diligent research to solve the above problems, and obtained novel crystal I by adding ethyl acetate/tert-butyl methyl ether to a crude product of compound (1). Also, the inventors have succeeded in obtaining novel crystal II by recrystallizing compound (1) at room temperature or a higher temperature using a general-purpose organic solvent such as an ester or ketone solvent. Specifically, the inventors have found the present novel crystals I and II having superior absorbability and storage stability, found that crystal II in particular is a crystal which can be obtained in a highly reproducible manner, and accomplished the present invention.

More specifically, the present invention provides [1] to [10] below.

[1] A crystal of (R)—N-(1-(3-(cyclopentyloxy)phenyl)ethyl)-3-((2,4-dioxo-3,4-dihydropyrimidin-1(2H)-yl)methoxy)propane-1-sulfonamide.

[2] The crystal according to [1] above, which is a crystal having at least two or more diffraction angle ($2\theta\pm0.2°$) peaks selected from 7.3°, 11.8°, 14.5°, 14.8°, 16.8°, 17.5°, 18.6°, 19.5°, 20.4°, 23.9°, 24.4°, 25.7°, 26.8°, and 31.5° in a powder X-ray diffraction spectrum.

[3] The crystal according to [1] or [2] above, which is a crystal having at least five or more diffraction angle ($2\theta\pm0.2°$) peaks selected from 7.3°, 11.8°, 14.5°, 14.8°, 16.8°, 17.5°, 18.6°, 19.5°, 20.4°, 23.9°, 24.4°, 25.7°, 26.8°, and 31.5° in a powder X-ray diffraction spectrum.

[4] The crystal according to any one of [1] to [3] above, having an endothermic peak at 108° C.±5° C. in differential scanning calorimetry.

[5] The crystal according to any one of [1] to [4] above, having the below crystal data obtained by single crystal analysis of the crystal:
Crystal system: Orthorhombic system
Space group: $P2_12_12_1$ (No. 19)
Lattice constant: a=9.3998(5) Å
b=10.3585(5) Å
c=23.5111(10) Å
Unit cell volume: 2289.22(19) Å$^3$
Z value: 4.

[6] A pharmaceutical composition comprising the crystal according to any one of [1] to [5] above.

[7] A pharmaceutical composition for oral administration, comprising the crystal according to any one of [1] to [5] above.

[8] Use of the crystal according to any one of [1] to [5] above for producing a pharmaceutical composition.

[9] The use according to [8], wherein the pharmaceutical composition is a pharmaceutical composition for oral administration.

[10] The crystal according to any one of [1] to [5] above for use as a medicine.

Advantageous Effect of the Invention

According to the present invention, a novel crystal of compound (1) having superior absorbability and storage stability can be obtained in a highly reproducible manner, and can be utilized as a drug substance for use in the production of a medicine.

DETAILED DESCRIPTION OF THE INVENTION

Figure 1:
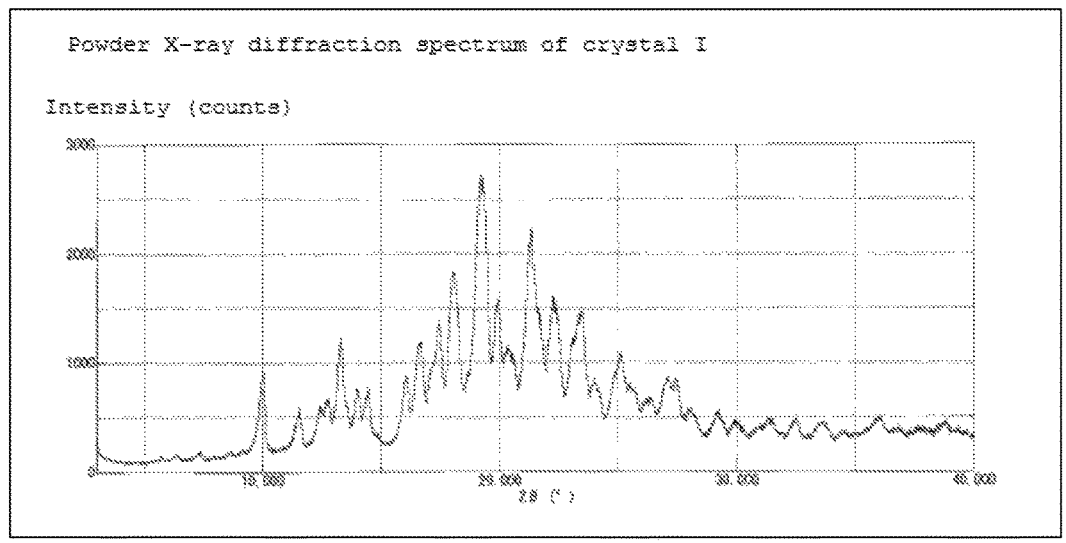
FIG. 1 shows a powder X-ray diffraction spectrum of crystal I (with the vertical axis indicating intensity (counts), and the horizontal axis indicating diffraction angle (2θ±0.2°)).

Hereinafter, the present invention will now be described in detail.

The present invention relates to a crystal of compound (1). There are two crystal forms of compound (1) in the present invention, i.e., crystal I and crystal II. While both have superior oral absorbability and stability, crystal II among these is more preferable also in terms of reproducibility when obtaining a crystal.

As used herein, the term "crystal" is used in its ordinary sense, and means a solid having a spatially regular atomic arrangement. Whether the solid is a crystal or not can be verified by an X-ray diffraction spectrum.

As for the powder X-ray diffraction pattern, diffraction angles and the overall pattern are important when recognizing the identity of a crystal due to the nature of the data. The relative intensity of the powder X-ray diffraction pattern can vary to some extent depending on the direction of crystal growth, the particle size, and the measurement conditions, and therefore it should not be interpreted in a strict sense.

There may be some variations in the numerical values obtained from various patterns depending on, for example, the direction of crystal growth, the particle size and the measurement conditions. Accordingly, as used herein, the term diffraction angle (2θ±0.2°) in a powder X-ray diffraction pattern means that it may be within the range of ±0.2° of that value.

The crystal of compound (1) of the present invention can be produced by crystallization of compound (1) in an amorphous form, or crystallization or recrystallization from the reaction product after synthesizing compound (1).

Compound (1) used in the crystallization method of the present invention is, for example, what is produced in accordance with the method described in Patent Document 1. For crystallization, it is possible to use compound (1) which, after being synthesized, is retained as-is without being taken out as a crystal or which is temporarily taken out as a crystal (a crude crystal). In order for more enhanced crystal purity, it is preferable to use compound (1) which is temporarily taken out as a crystal. As a crystal to be temporarily taken out, crystal I and crystal II are both usable.

As crystallization solvents, usable single solvents are ester solvents such as ethyl acetate, n-propyl acetate, and butyl acetate, ketone solvents such as methyl ethyl ketone and methyl isopropyl ketone, and alcohol solvents such as methanol and ethanol. The amount (v/w) of solvent is preferably 5 times to 30 times, more preferably 5 times to 20 times, and even more preferably 7 times to 10 times than the amount of compound (1). It is desirable that the dissolution temperature is room temperature or from room temperature to the boiling point of the each solvent.

In order to promote crystallization, a suitable amount of crystal I, crystal II, or a mixture of both crystal forms may be added as a seed crystal. The amount of the seed crystal to be added is preferably 0.01 to 5 (w/v) % and more preferably 0.03 to 1 (w/v) % based on the amount of solvent. The crystal may be precipitated under stirring in order to shorten the crystal precipitation time and control the particle diameter.

The precipitated crystal can be isolated/purified from the dissolution solution or mixed solution by, for example, known separation/purification means such as filtration, washing with an organic solvent, or reduced-pressure drying. Examples of the organic solvent used in washing include lower alcohols, acetone, acetonitrile, tert-butyl methyl ether, ethyl acetate, n-propyl acetate, isopropyl acetate, pentane, and heptane.

Crystal I is obtained from compound (1) when crystallized using a mixed solvent of a good solvent such as an ester solvent or a ketone solvent with a poor solvent such as an ether solvent. On the other hand, crystal II is obtained via recrystallization with a single solvent composed of an ester solvent or a ketone solvent, which is a good solvent. Crystal II can be obtained in a far more reproducible manner than crystal I.

It is preferable that crystal II is precipitated by adding a solvent such as an ester or ketone solvent to compound (1), heating the solvent to dissolve the compound, and then allowing the solution to be cooled or slowly cooling the solution for precipitation. The amount (v/w) of solvent used is preferably 5 times to 30 times, moreover 5 times to 20 times, and moreover 7 times to 10 times than the amount of compound (1).

Crystal I of the present invention thus obtained has a powder X-ray diffraction spectrum as shown in FIG. 1 and has a crystal structure. Characteristic diffraction angles (2θ±0.2°) of crystal I are two or more, preferably four or more, more preferably six or more, and even more preferably nine selected from the group consisting of 10.0°, 13.3°, 18.0°, 19.2°, 19.9°, 21.3°, 22.4°, 23.5°, and 25.1°.

The term "in the vicinity of" used in conjunction with the peak temperature of the endothermic peak in a differential scanning calorimetry (DSC) curve means a value approximately at that temperature, and preferably means that the temperature may be within the range of ±5° C. of that value, and more preferably means that the temperature may be within the range of ±2° C. of that value.

Figure 2:
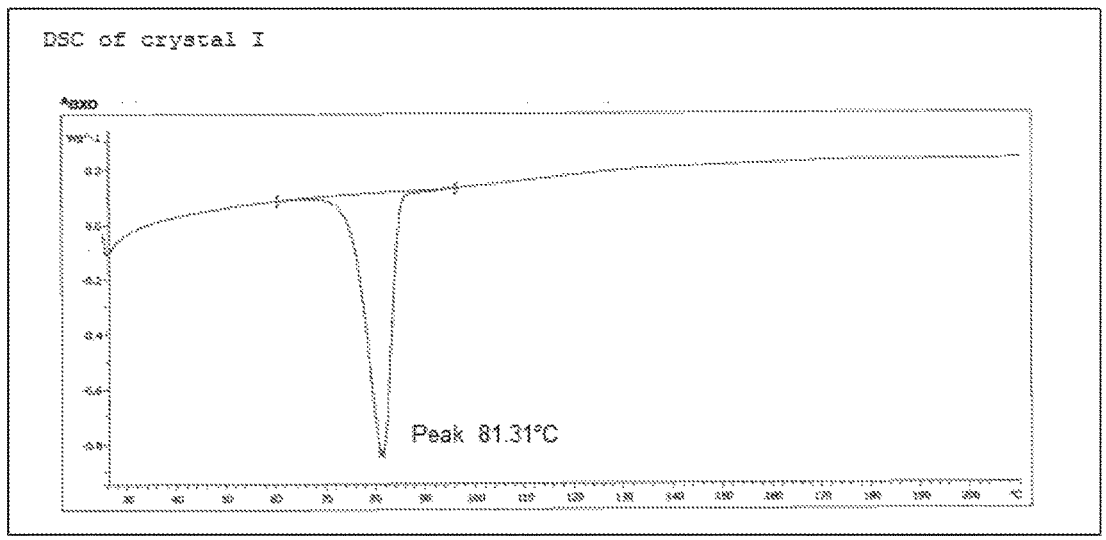
FIG. 2 shows a differential scanning calorimetry (DSC) curve of crystal I.

The differential scanning calorimetry (DSC) curve of crystal is shown in FIG. 2. According to FIG. 2, crystal I has an endothermic peak in the vicinity of 81±5° C.

Figure 3:
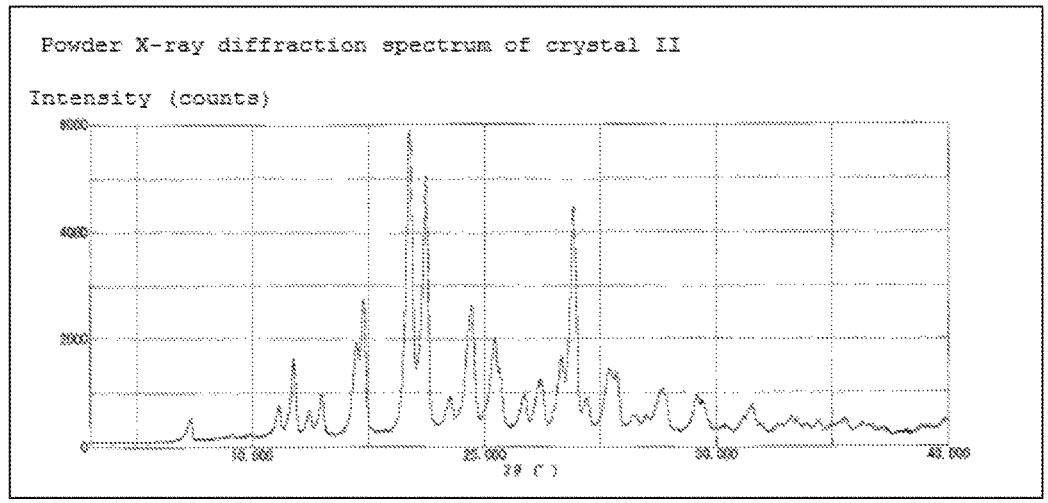
FIG. 3 shows a powder X-ray diffraction spectrum of crystal II (with the vertical axis indicating intensity (counts), and the horizontal axis indicating diffraction angle (2θ±0.2°)).

Crystal II has a powder X-ray diffraction spectrum as shown in FIG. 3. Characteristic diffraction angles (2θ±0.2°) of crystal II are at least two or more, more preferably four or more, even more preferably five or more, even more preferably eight or more, and even more preferably 14 selected from 7.3°, 11.8°, 14.5°, 14.8°, 16.8°, 17.5°, 18.6°, 19.5°, 20.4°, 23.9°, 24.4°, 25.7°, 26.8°, and 31.5°.

Figure 4:
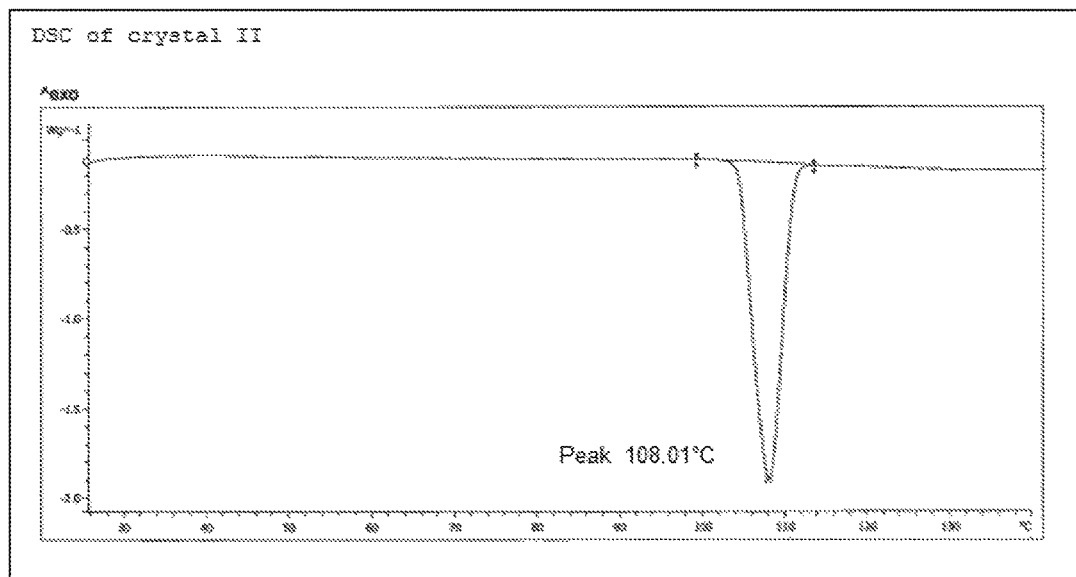
FIG. 4 shows a differential scanning calorimetry (DSC) curve of crystal II.

The differential scanning calorimetry (DSC) curve of crystal II is shown in FIG. 4. According to FIG. 4, crystal II has an endothermic peak in the vicinity of 108° C.±5° C.

It has become clear that crystal I and crystal II both have high oral absorbability. Among these, crystal II has particularly high oral absorbability.

Moreover, it has become clear that none of crystal I and crystal II has lowered purity even after long-term storage under light exposure, and both have high storage stability. Among these, crystal II has particularly high storage stability.

Thus, crystal I and crystal II both have high oral absorbability and long-term storage stability, and are useful as pharmaceutical ingredients of pharmaceutical compositions for oral administration. In particular, crystal II has superior oral absorbability and long-term storage stability and, also, has superior reproducibility when obtaining the crystal.

Crystal I or crystal II of the present invention can be formulated into various forms of pharmaceutical compositions with or without milling, e.g., oral preparations such as tablets, capsules, granules, fine granules, powders, and dry syrups, external preparations such as suppositories, inhalants, nasal drops, ointments, plasters, and aerosols, and injection preparation, and it is preferable to utilize it for an oral preparation. These pharmaceutical compositions can be produced using pharmaceutically acceptable carriers by commonly used preparation methods known to people skilled in the art. In the case of preparing an oral solid preparation, for example, an diluent and optionally a binder, a disintegrator, a lubricant, a coloring agent, a taste improving agent and a flavor improving agent are added to the active ingredient, and then, for example, a tablet, a coated tablet, a granule, a powder, a dry syrup or a capsule can be produced by an ordinary method. In the case of preparing an oral liquid preparation, for example, a taste improving agent, a buffer, a stabilizer and a flavor improving agent, are added to the active ingredient, and, for example, an oral solution or a syrup can be produced by an ordinary method. In the case of preparing an injection preparation, for example, a pH adjuster, a buffer, a stabilizer, an isotonizing agent and a topical anesthetic are added to the active ingredient, and a subcutaneous, intramuscular, or intravenous injection preparation can be produced by an ordinary method. In the case of preparing a rectal suppository, for example, an excipient and optionally a surfactant are added to the active ingredient, and then a suppository can be produced by an ordinary method. In the case of preparing an ointment in the form of, for example, paste, cream, and gel, a commonly used base, stabilizer, wetting agent and preservative are added as necessary, and then mixed and formulated by an ordinary method. Usable bases are, for example, white petrolatum, paraffin, glycerin, cellulose derivatives, polyethylene glycol, silicone and bentonite. Usable preservatives are, for example, methyl paraoxybenzoate, ethyl paraoxybenzoate and propyl paraoxybenzoate. In the case of preparing a patch, for example, the aforementioned ointment, cream, gel or paste is applied to a commonly used support by an ordinary method. A suitable support is, for example, woven or non-woven fabric made of cotton, staple fiber, or chemical fiber, or film or foamed sheet made of flexible polyvinyl chloride, polyethylene or polyurethane.

These pharmaceutical compositions are useful as, for example, antitumor effect potentiators for other antitumor agents (Patent Document 2).

The amount of crystal I or crystal II to be contained in the above pharmaceutical compositions varies depending on the symptom of a patient to which it is applied or depending on, for example, the dosage form. Generally, the amount is desirably about 5 to 1,000 mg for oral preparations, about 0.1 to 500 mg for injection preparation, and about 5 to 1,000 mg for suppositories or external preparations, per unit dosage form. Also, the daily dosage of crystal I or crystal II in the above pharmaceutical compositions cannot be generally determined according to, for example, the symptom, the administration route or the age of a patient, and is determined at the discretion of a physician. Normally, the amount is preferably about 0.1 to 5,000 mg.

EXAMPLES

Although the present invention is hereinafter described in more detail by way of Examples, the present invention is not limited thereto in any way. Although the present invention is sufficiently described by way of Examples, it should be understood that a person skilled in the art can make various changes and modifications. Accordingly, such changes and modifications are encompassed within the present invention as long as they do not depart from the scope of the present invention.

Various reagents used in the Examples were commercially available products unless stated otherwise. NMR spectra were measured with AL 400 (400 MHz; JEOL Ltd.), a Mercury 400 (400 MHz; Agilent Technologies, Inc.) spectrometer, or an Inova 400 (400 MHz; Agilent Technologies, Inc.) spectrometer equipped with a 400 MNMR probe (Protasis) using tetramethylsilane as an internal reference when tetramethylsilane was contained in a deuterated solvent or using an NMR solvent as an internal reference in other cases, and all $\delta$ values were expressed in ppm.

Abbreviations have the following meanings.
s: Singlet
d: Doublet
dd: Double doublet
m: Multiplet
brs: Broad singlet
Powder X-ray diffraction measurement
Powder X-ray diffraction was measured under the following test conditions after a suitable amount of test substance was lightly milled with an agate mortar as necessary.
Apparatus: Rigaku MiniFlex II
Target: Cu
X-ray output setting: 15 mA, 30 kV
Scan range: 2.0 to 40.0°
Step size: 0.010°
Scan speed: 5.00°/min.
Divergence slit: 1.25°
Scattering slit: Open
Receiving slit: Open
The apparatuses, including the apparatus for data processing, were handled according to the processes and procedures instructed for the apparatuses.

Numerical values obtained from various spectra may slightly vary depending on, for example, the direction of crystal growth, the particle size and the measurement conditions. Accordingly, those numerical values should not be interpreted in a strict sense.

Thermometric measurement (Differential scanning calorimetry measurement (DSC measurement))

DSC measurement was carried out under the following test conditions.
Apparatus: TA Instruments Q1000
Sample: Approximately 1 mg
Sample container: Made of aluminum
Heating rate: Heating to 300° C. at 10° C./min Atmospheric gas: Nitrogen Flow rate of nitrogen gas: 50 mL/min.

The apparatuses, including the apparatus for data processing, were handled according to the processes and procedures instructed for the apparatuses.

Example 1

Synthesis of (R)—N-(1-(3-(cyclopentyloxy)phenyl)ethyl)-3-((2,4-dioxo-3,4-dihydropyrimidin-1(2H)-yl)methoxy)propane-1- sulfonamide (Crystal I)

Ethyl acetate (16 mL) was added to a crude product (9.1 g) of compound (1), which had been synthesized by the known procedure disclosed in Patent Document 1, to dissolve the compound. Thereafter, tert-butyl methyl ether (160 mL) was slowly added dropwise, the mixture was stirred at room temperature for 15 hours, and thus crystal I of compound (1) was obtained as white powder (Yield: 7.9 g, 87.0%). As shown in the powder X-ray diffraction spectrum of FIG. 1, principal 2θ peaks were 10.0°, 13.3°, 18.0°, 19.2°, 19.9°, 21.3°, 22.4°, 23.5°, and 25.1°. As shown in the differential scanning calorimetry (DSC) curve of FIG. 2, the endothermic peak was 81.3° C.

$^1$H-NMR (CDCl$_3$): δ ppm 1.53 (3H, d, J=6.8 Hz), 1.56-1.98 (10H, m), 2.67-2.78 (1H, m), 2.80-2.91 (1H, m), 3.42-3.60 (2H, m), 4.51-4.63 (1H, m), 4.74-4.89 (2H, m), 5.05 (2H, s), 5.76 (1H, dd, J=7.8 Hz, 2.2 Hz), 6.77-6.89 (3H, m), 7.20-7.27 (2H, m), 8.76 (1H, brs):

LRMS (ESI) m/z 452 [M+H]

Example 2

Synthesis of (R)—N-(1-(3-(cyclopentyloxy)phenyl)ethyl)-3-((2,4-dioxo-3,4-dihydropyrimidin-1(2H)-yl)methoxy)propane-1-sulfonamide (Crystal II)

Butyl acetate (5 mL) was added to a crude product (500 mg) of compound (1), which had been synthesized by the known procedure disclosed in Patent Document 1, and thereafter the compound was completely dissolved using an oil bath set at 70° C. and then allowed to be cooled in air. White solids were precipitated at an inner temperature of 45° C., collected by filtration, and dried by being heated under reduced pressure for 20 hours, and crystal II of compound (1) was thus obtained as white powder (Yield: 412.5 mg, 82.5%). As shown in the powder X-ray diffraction spectrum of FIG. 3, principal 2θ peaks were 7.3°, 11.8°, 14.5°, 14.8°, 16.8°, 17.5°, 18.6°, 19.5°, 20.4°, 23.9°, 24.4°, 25.7°, 26.8°, and 31.5°. As shown in the differential scanning calorimetry (DSC) curve of FIG. 4, the endothermic peak was 108.0° C.

$^1$H-NMR (CDCl$_3$): δ ppm 1.53 (3H, d, J=6.8 Hz), 1.56-1.98 (10H, m), 2.67-2.78 (1H, m), 2.80-2.91 (1H, m), 3.42-3.60 (2H, m), 4.51-4.63 (1H, m), 4.74-4.89 (2H, m), 5.05 (2H, s), 5.76 (1H, dd, J=7.8 Hz, 2.2 Hz), 6.77-6.89 (3H, m), 7.20-7.27 (2H, m), 8.76 (1H, brs):

LRMS (ESI) m/z 452 [M+H]

Example 3

Single Crystal Analysis of (R)—N-(1-(3-(cyclopentyloxy)phenyl)ethyl)-3-((2,4-dioxo-3,4-dihydropyrimidin-1(2H)-yl)methoxy)propane-1-sulfonamide (Crystal II)

(R)—N-(1-(3-(cyclopentyloxy)phenyl)ethyl)-3-((2,4-dioxo-3,4-dihydropyrimidin-1(2H)-yl)methoxy)propane-1-sulfonamide was thermally dissolved in a water/methanol mixture (1:1) and left to stand at room temperature, and thus precipitation of single crystals of crystal II was confirmed.

Crystal size: 0.26×0.20×0.08 mm

Crystal color: Colorless

Crystal form: Columnar crystal

Measurement was carried out under the following measurement conditions, and data processing was carried out using structural analysis software Crystal Structure (Ver.3.8.2) manufactured by Rigaku Corporation.

Diffraction apparatus: Rigaku RAXIS-RAPID

Incident X ray: CuKα radiation (λ=1.54187 Å)

Crystal monochromator (graphite) was used

Output 50 kV, 100 mA

Collimator diameter: 0.5 mmφ

Detector: Imaging plate (460 mm×256 mm)

Scanning method: ω-2θ scan

Scanning speed: 1.0°/min (in omega)

2θmax: 143.5°

Number of measured reflections: 43629

Number of independent reflections: 4392 (Rint=0.020)

Data correction: Lorentz factor

Absorption correction: Correction by Ψ scan (Correction coefficient: 0.687 to 0.879)

Measurement temperature: About −180° C. (nitrogen gas spraying)

Crystal data is shown below.

Crystal system: Orthorhombic system

Space group: P2$_1$2$_1$2$_1$ (No. 19)

Lattice constant: a=9.3998 (5) Å b=10.3585(5) Å c=23.5111(10) Å

Unit cell volume: 2289.22(19) Å$^3$

Z value: 4

Test Example 1

Blood Concentration Measurement Test

A 0.5% HPMC dosing suspension (50 mg/10 mL/kg) of each of crystal I and crystal II was prepared. These suspensions were orally administered to mice (Balb/cA), which had been reared under feeding conditions, in a volume of 10 mL per kg body weight using an oral gavage tube. After administration, mice were returned to the mouse cage, and their conditions were checked. In the cage, water and feed were available ad libitum. At 0.5, 1, 2, 4, 6, and 8 hours after administration, mice were anesthetized with isoflurane, and 60 µL of blood was collected from the orbital venous plexus using a capillary blood collecting tube. The collected blood was ice-cooled, and centrifuged to separate plasma. The mice after blood collection were returned to the animal rearing cage, and their conditions after recovering from anesthesia were checked. After the final blood collection, the depth of isoflurane anesthesia was checked, and then the mice were euthanized by cervical dislocation.

From the concentrations of compound (1) in plasma measured by MRM method using LC-MS/MS, AUC$_{0-24}$ hr was calculated by log-linear trapezoidal method using Phoenix WinNonlin (v6.3.0), software manufactured by Pharsight.

Results are shown in Table 1. From this test, it was found that crystal II shows an AUC$_{0-24\ hr}$ (the area under blood concentration-time curve 0 to 24 hours after administration) value similar to that of crystal I. It was thus verified that crystal II according to the present invention, which has preferable oral absorbability and can be obtained in a highly reproducible manner, can be secured.

TABLE 1

| Parameter | Oral administration | |
|---|---|---|
| | Crystal I | Crystal II |
| $AUC_{0-24\,hr}$ (μM · hr) | 122.16 | 144.51 |

Test Example 2

Solid Stability Test (Under Light Exposure)

The solid stabilities of crystal I and crystal II obtained in the Examples, when stored for 1 month under light exposure, were measured under the following conditions.

Storage condition: Sample was placed in a transparent glass bottle, then the lid was placed, and the grove between the lid and the bottle was sealed by the grafting tape.
  Measurement point: 1 Month
  Stored amount: About 30 mg
  Storage container: Clear glass bottle
  Chemical purity of compound (1) in the sample solution was measured by HPLC analysis. The apparatuses, including the apparatus for data processing, were handled according to the processes and procedures instructed for the apparatuses. (Apparatus: Shimadzu Corporation LC-20AB)
  Column: L-column 2 ODS manufactured by Chemicals Evaluation and Research Institute, 4.6×150 mm, 5 μm
  UV detection: 220 nm
  Column temperature: 50° C.
  Column flow rate: 1.0 mL/min
  Mobile phase: A; Water, B; Acetonitrile
  Injection amount: 10 μL
  Sample concentration: 1.0 mg/mL
  Gradient: Table 2

TABLE 2

| Time(min) | A | B |
|---|---|---|
| 0-10 | 65% → 60% | 35% → 40% |
| 10-30 | 60% → 10% | 40% → 90% |

Figure 5:
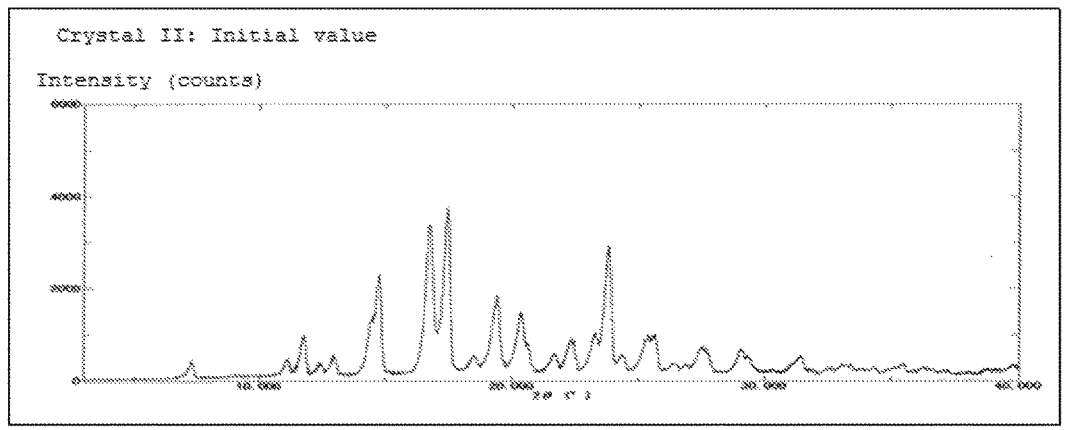
FIG. 5 shows a powder X-ray diffraction spectrum of crystal II before a solid stability test (under light exposure) (with the vertical axis indicating intensity (counts), and the horizontal axis indicating diffraction angle (2θ±0.2°)).
Figure 6:
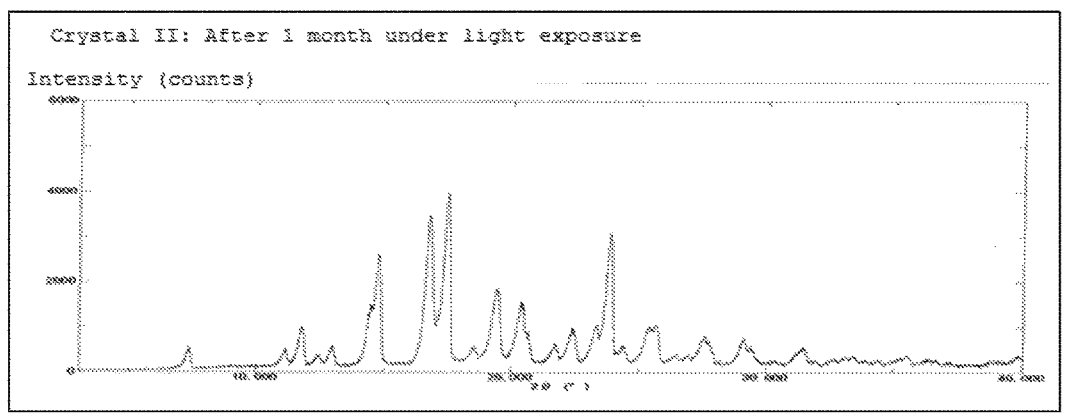
FIG. 6 shows a powder X-ray diffraction spectrum of crystal II after a solid stability test (under light exposure) (with the vertical axis indicating intensity (counts), and the horizontal axis indicating diffraction angle (2θ±0.2°)).

The chemical purity results of compound (1) measured are shown in Table 3. The chemical purities of crystal I and crystal II did not change for 1 month under light exposure, and also the results of powder X-ray crystallography revealed no change of crystal form (FIG. 5 and FIG. 6).

TABLE 3

| | Chemical purity(%) | |
|---|---|---|
| | Initial value | One month later |
| Crystal I | 97.8 | 97.4 |
| Crystal II | 99.0 | 99.1 |

The invention claimed is:

1. A crystal of (R)—N-(1-(3-(cyclopentyloxy)phenyl)ethyl)-3-((2,4-dioxo-3,4-dihydropyrimidin-1(2H)-ly)methoxy)propane-1-sulfonamide, having at least five diffraction angle (2θ±0.2°) peaks selected from the group consisting of 7.3°, 11.8°, 14.5°, 14.8°, 16.8°, 17.5°, 18.6°, 19.5°, 20.4°, 23.9°, 24.4°, 25.7°, 26.8°, and 31.5° in a powder X-ray diffraction spectrum.

2. The crystal according to claim 1, having an endothermic peak at 108° C.±5° C. in differential scanning calorimetry.

3. The crystal according to claim 1, having crystal data shown below obtained by single crystal analysis of the crystal:
  Crystal system: Orthorhombic system
  Space group: $P2_12_12_1$ (No. 19)
  Lattice constant: a=9.3998(5) Å
  b=10.3585(5) Å
  c=23.5111(10) Å
  Unit cell volume: 2289.22(19) Å$^3$
  Z value: 4.

4. A pharmaceutical composition comprising the crystal according to claim 1.

5. A pharmaceutical composition comprising the crystal according to claim 1, wherein the pharmaceutical composition is suitable for oral administration.

6. A pharmaceutical composition which potentiates the antitumor effect of an antitumor drug, comprising the crystal of claim 1 and one or more pharmaceutically acceptable excipients.

7. The crystal according to claim 1, having at least eight diffraction angle (2θ±0.2°) peaks selected from the group consisting of 7.3°, 11.8°, 14.5°, 14.8°, 16.8°, 17.5°, 18.6°, 19.5°, 20.4°, 23.9°, 24.4°, 25.7°, 26.8°, and 31.5° in a powder X-ray diffraction spectrum.

8. The crystal according to claim 1, haying at least the diffraction angle (2θ±0.2° peaks of 7.3°, 11.8°, 14.5°, 14.8°, 16.8°, 17.5°, 18.6°, 19.5°, 20.4°, 23.9°, 24.4°, 25.7°, 26.8°, and 31.5° in a powder X-ray diffraction spectrum.

* * * * *